US012602554B2

(12) United States Patent
　Fridman

(10) Patent No.:　US 12,602,554 B2
(45) **Date of Patent:　*Apr. 14, 2026**

(54) SYSTEMS AND METHODS FOR PRODUCING RELIABLE TRANSLATION IN NEAR REAL-TIME

(71) Applicant: Language Scientific, Inc., Medford, MA (US)

(72) Inventor: Leonid Fridman, Newton, MA (US)

(73) Assignee: Language Scientific, Inc., Medford, MA (US)

( * ) Notice: Subject to any disclaimer, the term of this patent is extended or adjusted under 35 U.S.C. 154(b) by 217 days.

This patent is subject to a terminal disclaimer.

(21) Appl. No.: 18/512,723

(22) Filed: Nov. 17, 2023

(65) Prior Publication Data

US 2024/0086649 A1　Mar. 14, 2024

Related U.S. Application Data

(63) Continuation-in-part of application No. 15/969,417, filed on May 2, 2018, now Pat. No. 11,836,454.

(51) Int. Cl.
　*G06F 40/51*　(2020.01)
　*G06F 40/58*　(2020.01)
　*G16H 40/20*　(2018.01)
(52) U.S. Cl.
　CPC .............. *G06F 40/51* (2020.01); *G06F 40/58* (2020.01); *G16H 40/20* (2018.01)
(58) Field of Classification Search
　CPC .......... G06F 40/51; G06F 40/58; G06F 40/30; G16H 40/20; G16H 20/10; G16H 40/67
　See application file for complete search history.

(56) References Cited

U.S. PATENT DOCUMENTS 5,528,491 A　6/1996　Kuno et al.
6,330,530 B1　12/2001　Horiguchi et al.
(Continued)

FOREIGN PATENT DOCUMENTS

WO　WO-2018073635 A1　4/2018

OTHER PUBLICATIONS

Pease et al., "Towards an Automatic Translation of Medical Terminology and Texts into Arabic," Transltaion in the Abrab World, King Fahd Advanced School of Translation Tangier (1996).
(Continued)

*Primary Examiner* — Michael N Opsasnick
(74) *Attorney, Agent, or Firm* — Goodwin Procter LLP

(57)　ABSTRACT

A computer-implemented method is provided for translating input text from a source language to a target language including receiving, by an interface, the input text in a source language, and identifying, by a processor coupled to the interface, at least one portion of the input text. The method includes replacing each portion with a corresponding sematic structure to produce at least one semantic structure, and organizing the at least one semantic structure into a semantic tree. The method includes matching a portion of the semantic tree to at least one phrase from a stored phrase bank, and providing one or more versions of the at least one phrase in the source language. The method includes receiving a selected version of the set of versions, translating the selected version from the source language to the target language, and providing the selected version in the target language.

18 Claims, 6 Drawing Sheets

(56) References Cited

U.S. PATENT DOCUMENTS

| | | | |
|---|---|---|---|
| 7,584,103 | B2 | 9/2009 | Fritsch et al. |
| 7,974,831 | B2 | 7/2011 | Kamatani et al. |
| 8,086,468 | B2 * | 12/2011 | Kim ....................... G16H 70/20 |
| | | | 705/2 |
| 8,249,858 | B2 | 8/2012 | Bodin et al. |
| 8,473,971 | B2 | 6/2013 | Meijer et al. |
| 11,836,454 | B2 * | 12/2023 | Fridman ................. G06F 40/58 |
| 2004/0111272 | A1 | 6/2004 | Gao et al. |
| 2005/0010394 | A1 * | 1/2005 | Bergeron ................ G06F 40/30 |
| | | | 705/2 |
| 2005/0010428 | A1 * | 1/2005 | Bergeron ........... G06Q 30/0601 |
| | | | 705/26.1 |
| 2005/0033605 | A1 * | 2/2005 | Bergeron ............... G16H 40/20 |
| | | | 705/26.1 |
| 2005/0209885 | A1 | 9/2005 | Lamb et al. |
| 2005/0261910 | A1 | 11/2005 | Precoda et al. |
| 2006/0041428 | A1 * | 2/2006 | Fritsch ................ G10L 15/1815 |
| | | | 704/E15.024 |
| 2006/0122865 | A1 | 6/2006 | Preiss et al. |
| 2006/0129381 | A1 | 6/2006 | Wakita |
| 2006/0247968 | A1 * | 11/2006 | Kadry ................. G06Q 30/0255 |
| | | | 705/2 |
| 2007/0055978 | A1 | 3/2007 | Meijer et al. |
| 2008/0040095 | A1 | 2/2008 | Sinha et al. |
| 2008/0086298 | A1 | 4/2008 | Anismovich et al. |
| 2009/0048869 | A1 * | 2/2009 | Tyler ....................... G16H 40/63 |
| | | | 370/310 |
| 2010/0010804 | A1 | 1/2010 | Friedman et al. |
| 2010/0324936 | A1 * | 12/2010 | Vishnubhatla ......... G06Q 40/08 |
| | | | 715/810 |
| 2011/0010163 | A1 | 1/2011 | Jansen |
| 2011/0307274 | A1 | 12/2011 | Thompson et al. |
| 2012/0078763 | A1 * | 3/2012 | Koll ....................... G06Q 30/04 |
| | | | 705/34 |
| 2012/0173257 | A1 | 7/2012 | Preiss et al. |
| 2012/0215560 | A1 | 8/2012 | Ofek et al. |
| 2012/0303388 | A1 | 11/2012 | Vishnubhatla et al. |
| 2012/0330665 | A1 | 12/2012 | Berkun |
| 2013/0006654 | A1 * | 1/2013 | Hermans ................ G16H 10/20 |
| | | | 705/2 |
| 2014/0142963 | A1 | 5/2014 | Hill et al. |
| 2014/0244309 | A1 | 8/2014 | Francois |
| 2015/0006143 | A1 | 1/2015 | Skiba et al. |
| 2015/0324547 | A1 * | 11/2015 | Graham ................. G16H 70/40 |
| | | | 705/2 |
| 2016/0048655 | A1 * | 2/2016 | Maitra ................... G16H 70/40 |
| | | | 705/3 |
| 2016/0321404 | A1 | 11/2016 | Ginsburg |
| 2017/0228517 | A1 | 8/2017 | Saliman et al. |
| 2017/0262614 | A1 | 9/2017 | Vishnubhatla et al. |
| 2021/0287800 | A1 * | 9/2021 | Ghosh ................... G16H 10/60 |
| 2024/0006039 | A1 * | 1/2024 | Ferrando .............. G06F 40/174 |
| 2024/0086649 | A1 * | 3/2024 | Fridman ............... G16H 40/67 |

OTHER PUBLICATIONS

Tietschert et al., "Translating the Patient Perception of Integrated Care Survey to Measure Integrated Care in the Netherlands: Combining Equivalence and Contextualization Approaches for Optimal Results," (14 pages) https://www.ijic.org/articles/10.5334/ijic.2022.

* cited by examiner

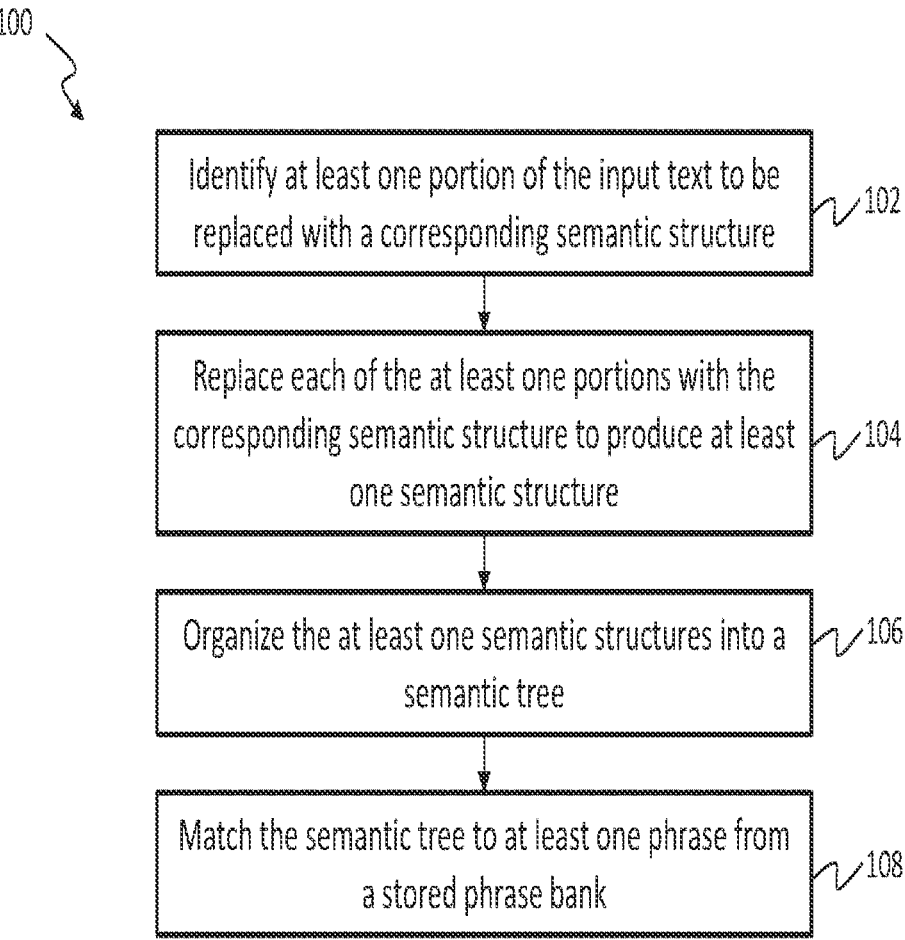

100

Identify at least one portion of the input text to be replaced with a corresponding semantic structure    102

Replace each of the at least one portions with the corresponding semantic structure to produce at least one semantic structure    104

Organize the at least one semantic structures into a semantic tree    106

Match the semantic tree to at least one phrase from a stored phrase bank    108

FIG. 1

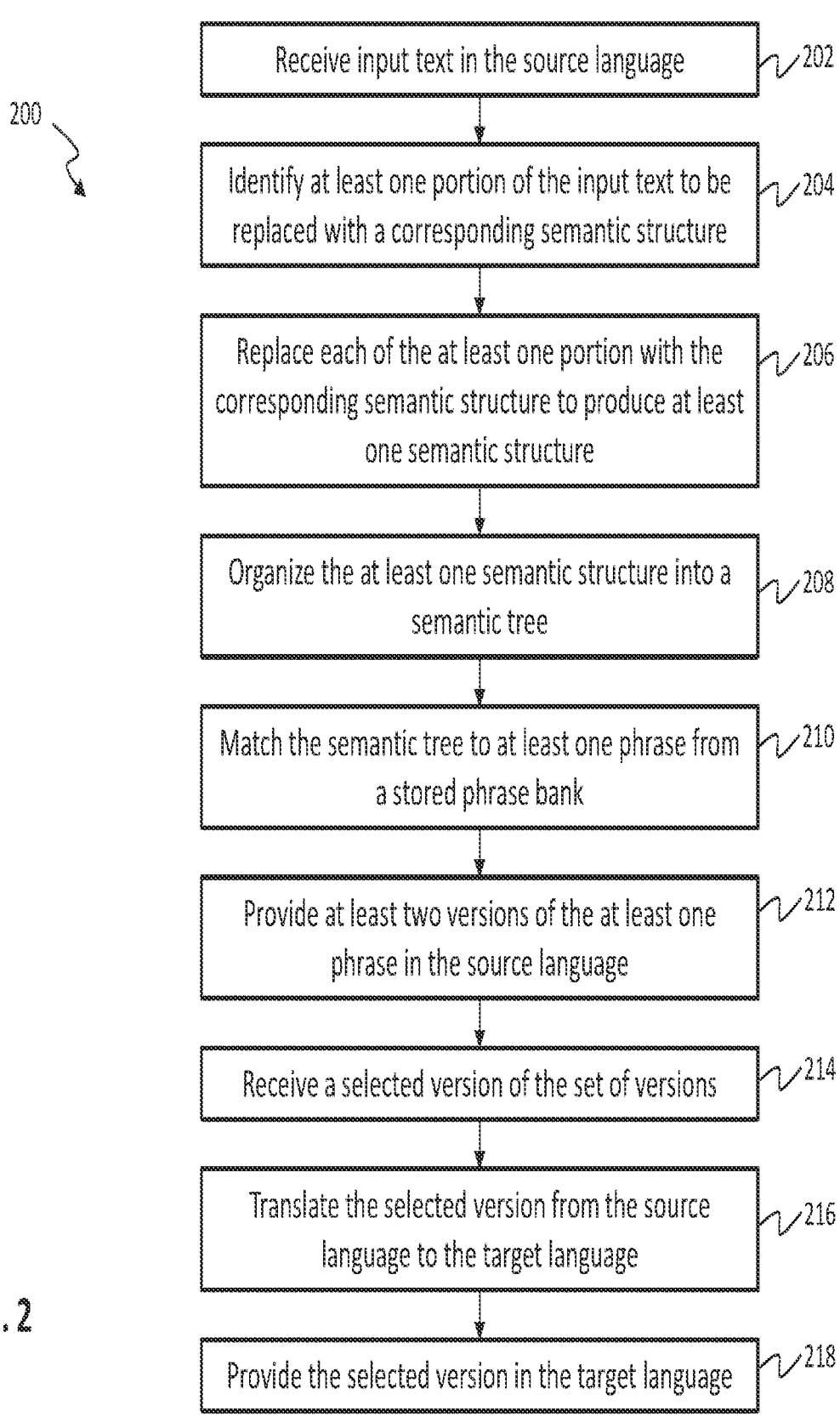

200

Receive input text in the source language          202

Identify at least one portion of the input text to be replaced with a corresponding semantic structure          204

Replace each of the at least one portion with the corresponding semantic structure to produce at least one semantic structure          206

Organize the at least one semantic structure into a semantic tree          208

Match the semantic tree to at least one phrase from a stored phrase bank          210

Provide at least two versions of the at least one phrase in the source language          212

Receive a selected version of the set of versions          214

Translate the selected version from the source language to the target language          216

Provide the selected version in the target language          218

TAKE <<NUM_0>> TABLETS BEFORE BEDTIME.

Translations: 506

SEM structure: 504

English: TAKE NUM_0 TABLETS BEFORE BEDTIME. 508a

INSTRUCTION_0 402

Spanish: TOMAR NUM_0 TABLETAS ANTES DE ACOSTARSE. 508b

SCHEDULE_1 406

Russian: ПРИНИМАТЬ NUM_0 ТАБЛЕТКИ (OK) ПЕРЕД СНОМ. 508c

Admin_Event_1 416

Vietnamese: UỐNG NUM_0 VIÊN TRƯỚC KHI NGỦ. 508d

Directive: take 432

Dose: NUM_0-tablets 434

Timing: type day_part: before_bedtime 436

SYSTEMS AND METHODS FOR PRODUCING RELIABLE TRANSLATION IN NEAR REAL-TIME

CROSS-REFERENCE TO RELATED APPLICATIONS

This application is a continuation-in-part of U.S. application Ser. No. 15/969,417, filed May 2, 2018, now U.S. Pat. No. 11,836,454, issued on Dec. 5, 2023, the contents of which are incorporated by reference herein in their entirety.

TECHNICAL FIELD

The following disclosure is directed to methods and systems for translating input text from a first language to a second language, and more specifically, methods and systems for translating input text from a first language to a second language in real-time or near real-time.

BACKGROUND

Present machine-based solutions for translating text from one language to another are often characterized by their speed and cost-effectiveness but not necessarily their accuracy. This is in contrast to human translators, which are slower and more expensive but have the benefit of increased accuracy. It is noted that even human translators may not agree on how to accurately translate particular phrases or terminology, even those translating in the same technical field. In many instances, quick machine translations are helpful and their accuracy may have little effect on outcomes for a particular purpose, such as translating a greeting in a foreign country. However, in many contexts, such as health-care or business practice, the accuracy of a translation can be significant to the desired outcome.

Specifically, in domains such as healthcare, even a low risk of inaccurate translation can be life-threatening and, therefore, unacceptable. For instance, an English-speaking pharmacist may dispense medication to a Spanish-speaking patient that does not understand English well. The pharmacist attaches prescription directions to a bottle of medicine that reads "Give half a teaspoon by mouth 3 times a day" in English. However, she wishes to give the patient the same directions in Spanish in a quick enough time. Among the options that exist are online translators, such as Google Translate, which are able to output a translation very quickly but lack context and sacrifice accuracy or reliability of their outputs to achieve the ease of use and speed. The pharmacist can never be sure that the translated output is accurate enough for the patient. The pharmacist may try to double-check the translated output (e.g., in Spanish) by "back-translating" or entering the output into the input to see the result in English. However, even when the translated output is translated back to the original language (in English) by the online translator, the online translator will often produce the original input text. This is because online translators are statistical machine translation programs that are trained on pairs of sentences, often leading to symmetrical results in either direction. Thus, "back-translating" does not solve the critical problem of a mistranslation.

Even if machine translation mistranslated medical directions for a fraction of the instances, the pharmacist cannot risk using machine translation because she does not know in any given case whether the translation is right or wrong. A materially wrong translation can be much worse than no translation at all; at least if there is no translation provided, the patient might find a friend or a family member to help interpret the instruction. If the patient has incorrect directions in her native language, she is likely to treat the pharmacist-issued translation as authoritative and use the medicine according to these directions without further checks.

Instead of a machine translator, interpreters may sometimes be employed for the purpose of translating medical directions to patients in person or by phone. However, there are drawbacks to involving interpreters in conveying important information, such as high costs and the lack of written directions to accompany the medication. Further, medical interpretation in real time or near-real time is also prone to relatively high error rates having potentially serious medical consequences. One reason for this is that, in contrast to textual translation, interpretation of oral communication cannot use references or edit their interpretations quickly enough for their purpose.

On the other end of the accuracy and temporal spectrum, there are translations that subscribe to the gold standard for translations. That is, the translation of text that requires a forward translation (from a first language to a second language), editing of the forward translation, back translation, and reconciliation (to eradicate discrepancies). However, this requires multiple professional linguists and cannot be performed in near real-time.

The problem described above is widespread in the United States, where in fact, approximately 22 million residents have limited English proficiency (LEP), leading to a situation faced daily by thousands of U.S. pharmacies. Similar scenarios occur in other industries, such as legal and technical environments, in which critical information can be easily mistranslated to the detriment of the recipient. Thus, a real need exists for verifiable translations in real-time or near real-time.

SUMMARY

In addition to the pharmacy scenario described above, the systems and techniques described herein can be adapted to a number of other fields in which the translation needs to be produced in near real-time but accuracy of the translation is paramount. Such fields include emergency communications, patient communications in hospitals and clinics, evacuation instructions, law enforcement, urgent legal communications, and the like. For instance, the users of the exemplary systems may be government or emergency services personnel who need to communicate urgent messages (e.g. evacuation instructions) to the population, which may include a substantial number of people who do not understand the source language. One significant advantage to the systems and methods described herein is that the user of the system that inputs text in a first language is able to check whether the translation into the second language will have his or her intended meaning even if the user herself does not know the second language, as will be described in more detail below. After the user agrees with the intended meaning, the systems and methods are able present a translation of the input text in the second language.

In accordance with an embodiment of the disclosure, a computer-implemented method is provided for translating input text of a medical prescription from a source language to a target language. The method includes receiving, by an interface, the input text in a source language, and identifying, by a processor coupled to the interface, a portion of the input text, each portion to be replaced with a corresponding semantic structure. The corresponding semantic structure is provided in a storage coupled to the processor. The method further includes replacing, by the processor, each portion with the corresponding sematic structure to produce at least one semantic structure, and organizing, by the processor, the at least one semantic structure into a semantic tree. The method further includes matching, by the processor, a portion of the semantic tree to at least one phrase from a stored phrase bank, and providing, by the interface, one or more versions of the phrase or phrases in the source language. The method further includes receiving, by the interface, confirmation of a selected version of the one or more versions; translating, by the processor, the confirmed version from the source language to the target language; and providing, by the interface, the selected version in the target language.

In a related embodiment, the interface is a user interface in which a user enters the input text and/or the confirmed version. In another related embodiment, the interface comprises an application programming interface (API) with an external computing system. Optionally, the external computing system comprises a pharmacy management system.

In another related embodiment, the method includes replacing, by the processor, numerical information in the input text with corresponding variables, and replacing, by the processor, the corresponding variables with the numerical information before providing, by the interface, the set of versions of the at least one phrase in the source language.

In yet another related embodiment, the method includes analyzing, by the processor, the input text for (a) incorrect grammar in the source language, (b) abbreviations, and/or (c) pharmacy codes; and replacing, by the processor, any portion of the input text that contains (a) incorrect grammar in the source language, (b) abbreviations, and/or (c) pharmacy codes, with a normalized substitute term.

In a further related embodiment, the method includes providing, by the interface, a set of target languages to translate a selected one of the one or more versions; receiving, by the interface, the selected target language from the set of target languages, and translating, by the processor, the confirmed version from the source language to the selected target language. Optionally, the method includes removing, by the processor, any unrecognized text in the input text before replacing, by the processor, each portion with the corresponding sematic structure to produce at least one semantic structure.

In another related embodiment, the matching, by the processor, the semantic tree to at least one phrase from the phrase bank further includes matching the semantic tree to a sequence of at least one phrase from the phrase bank. Optionally, the providing, by the interface, (i) one or more versions of the at least one phrase in the source language and (ii) a set of target languages to translate a selected one of the at least two versions, further includes providing, by the interface, (iii) an option to decline the at least two versions.

In a further related embodiment, the method includes compiling the phrases in the phrase bank prior to receiving input text in the source language. Optionally, each version at least one phrase, and wherein a commutative property applies to a sequence of the at least one phrase within the version. Optionally, the at least one semantic structures include at least one of a schedule semantic structure and indication semantic structure. Optionally, the schedule semantic structures includes at least one of an administrative substructure and a temporal substructure.

In yet another related embodiment, the method includes matching, by the processor, a portion of the semantic tree to one or more phrases from the stored phrase bank, and a first version of the at least two phrases has a first number of strings and a second version of the at least two phrases has a second number of strings, the first number of strings different than the second number of strings. Optionally, the first number is greater than the second number, and wherein the first version is ranked lower than the second version. In a related embodiment, providing, by the interface, at least two versions of the at least one phrase in the source language further includes providing, by the interface, at most four versions of the at least one phrase in the source language.

In a further related embodiment, the at least one semantic structure includes at least two semantic structures. The at least two semantic structures include a first semantic structure having a first property and a second semantic structure having a second property, and matching, by the processor, a portion of the semantic tree to at least one phrase from a stored phrase bank further includes selecting phrases from the phrase bank such that the first property does not contradict the second property.

In yet another related embodiment, the method further includes receiving, by the interface, modified input text in the source language; identifying, by the processor, at least one portion of the modified input text, each portion to be replaced with a different corresponding semantic structure, the corresponding semantic structure provided in a storage coupled to the processor; and replacing, by the processor, each of the at least one portion with the corresponding semantic structure to produce at least one semantic structures. The method further includes organizing, by the processor, the at least one semantic structures into a different semantic tree; matching, by the processor, a portion of the semantic tree to at least one phrase from the stored phrase bank; and providing, by the interface, (i) at least one modified version of the at least one phrase in the source language and (ii) at least one target language to translate the at least one modified version. The method further includes receiving, by the interface, a selected version of the modified set of versions and a selected target language from the set of target languages; translating, by the processor, the selected version from the source language to the target language; and providing, by the interface, the selected version in the target language. Optionally, the modified set of versions is mutually exclusive with the set of versions.

BRIEF DESCRIPTION OF THE DRAWINGS

FIG. 1 is a flowchart of an exemplary embodiment of a computer-implemented method for translating input text from a source language to a target language.

FIG. 2 is a flowchart of an exemplary embodiment of a computer-implemented method for translating input text from a source language to a target language.

DETAILED DESCRIPTION

Disclosed herein are exemplary embodiments of systems and methods for near real-time translations of input text in a first language into a second language. The approaches described allow the author of the input text in the first language to verify the resulting translation (in the second language), even if she does not speak or read in the second language. In the description of the embodiments below, the "first language" may be referred to as the "source language" and the "second language" may be referred to as the "target language." Likewise, the "input text" may be referred to as "source text" and "output text" may be referred to as "target text." Further, as described herein, the translation of an input in "near real-time" can include producing an output instantaneously or with a delay measured on the order of seconds or minutes after the input text has been received by the exemplary system or method.

Translation Framework

FIG. 1 is a high-level flowchart of an exemplary embodiment of a computer-implemented method 100 for translating input text from a source language to a target language. The method 100 includes step 102 in which at least one portion of an input text are identified so as to be replaced with a corresponding semantic structure. The identification of the at least one portion may typically be performed by a processor, as discussed in more detail below. Once identified, in step 104, each of the at least one portion are replaced with the corresponding semantic structure to product at least one semantic structures. In step 106, the at least one semantic structure is organized into a semantic tree. In step 108, the semantic tree is matched to at least one phrase from a stored phrase bank. As discussed in greater detail below, the phrase bank allows the processor to return translations to the user of the system in near real-time.

Illustration of Translation in Near Real-Time

To provide context for the exemplary methods and systems provided herein, FIGS. 2-5 will be discussed together in a medical setting, specifically in the context of a doctor or pharmacist, who speaks in a first language, providing directions for taking medicine to a patient, who speaks in a second language. It is understood that the methods and systems described herein can be used in entirely different settings and for entirely different purposes, such as in the legal, travel, or business industries.

Figure 3:
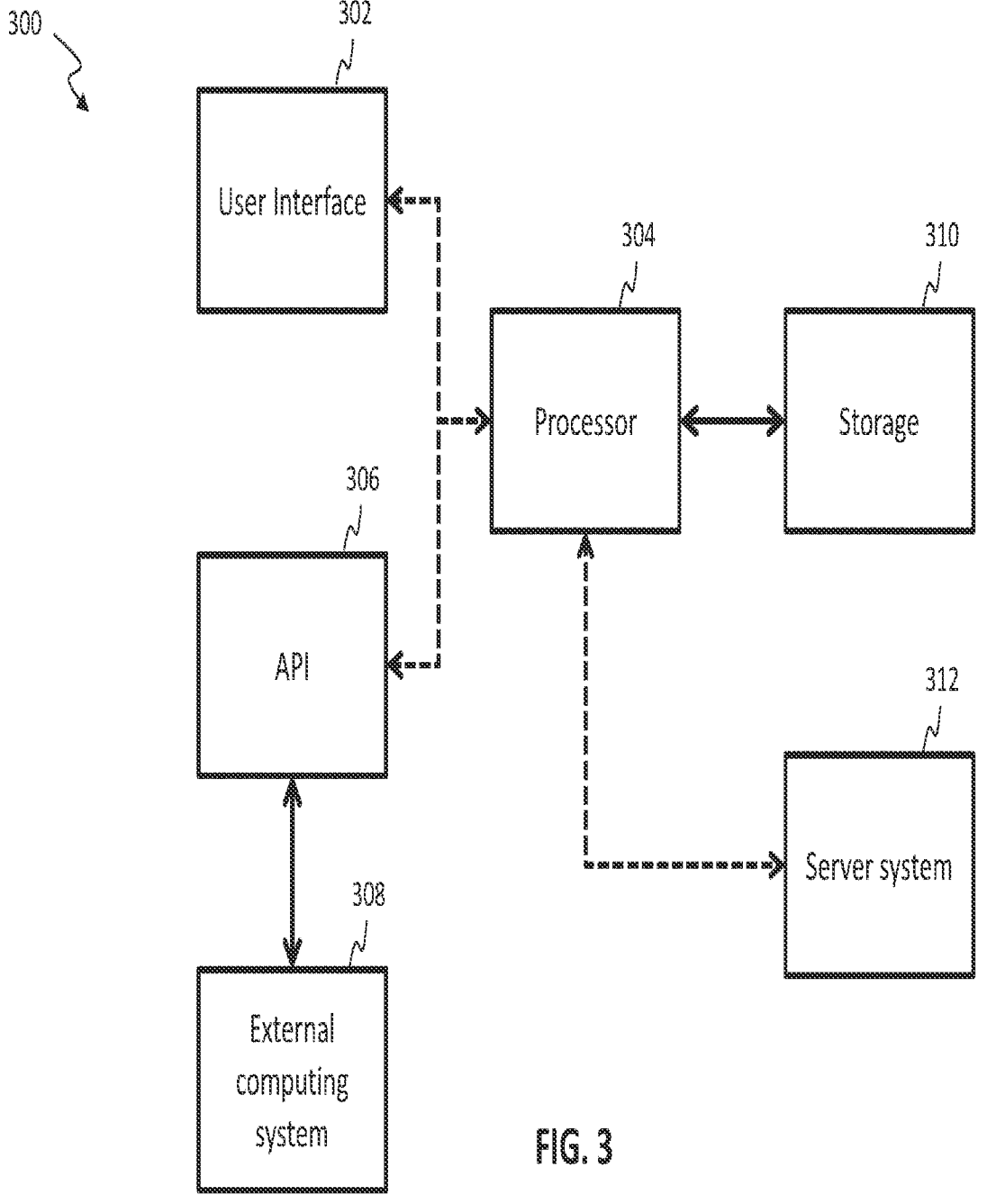
FIG. 3 is a diagram of an exemplary embodiment of a system for translating input text from a source language to a target language.

FIG. 2 is a flowchart of an exemplary embodiment of a computer-implemented method 200 for translating input text from a source language to a target language. FIG. 3 is a diagram of an exemplary embodiment of a system 300 for translating input text from a source language to a target language. The exemplary computer-implemented method 200, in step 202, receives input text in the source language. The input text may be entered by the user, in this example a pharmacist, into a user interface 302 coupled to processor 304. In another embodiment, an external computing system 308 provides the input text or instruction to the processor 304 via application programming interface (API) 306. For example, the external computing system 308 may be a pharmacy management system. In some embodiments, a user of the system may be able to speak into the user interface, which can be configured to process and convert the user's speech into the input text coupled to the processor 304. For instance the user interface may include one or more microphones that may be in communication with the processor 304, without limitation. The user interface may provide one or more graphical icons that may indicate when a user should speak into the user interface for speech to text synthesis. Graphical icons may include microphones, speech bubbles, and the like. The processor 304 may be configured to utilize one or more speech recognition algorithms, such as, but not limited to, Hidden Markov models (HMM), Dynamic time warping (DTW)-based speech recognition, and/or one or more neural networks. The processor 304 may receive through the user interface speech in the form of words, sentences, phrases, and the like. For example and without limitation, the processor 304 may receive four spoken sentences from a user that may be converted to text in real-time as the user is speaking An example of input text from a pharmacist is in the form of an instruction S:

Take 2 tablets now, then every day for the next 2 weeks, take 1 tablet in the morning and 2 tablets before bedtime for severe pain.

Note that the input text can take other forms. For instance, other examples of prescriptions include: "Take 1.5 tabs 3×/day" or "Give 2 teaspoons by mouth with breakfast, lunch, and dinner for 1 week, then 1 teaspoonful by mouth 3 times a week for the next 3 weeks." In pharmacy parlance, these directions for use are known as "sigs."

In an exemplary embodiment, the instruction is normalized to assign each numerical component of the instruction with a placeholder. Thus, a normalized instruction S norm appears as:

Take <<NUM_0>> tablets now, then every day for the next <<NUM_1>> weeks, take <<NUM_2>> tablet in the morning and <<NUM_3>> tablets before bedtime for severe pain.

Note that before the translation is returned to the user, these numerical placeholders are replaced with their original values. Optionally, the processor 304 may process the input text by, for example: correcting spelling, normalizing punctuation, normalizing cases, normalizing spelling (e.g., replacing "3$^{rd}$" with "third"), and/or expanding abbreviations, etc. For instance, in writing "sigs," doctors and pharmacists often use sig codes such as "tid" which means "3 times a day," "qd" which means "every day," "q34h" which means "every 3 to 4 hours," "po" which means "by mouth," "×7d" which means "for 7 days," etc. These sig codes are not standardized; different pharmacies and doctors use somewhat different versions of the sig codes. Therefore, a given sig may have several interpretations because it can be expanded using different sig codes. In some embodiments, the methods and systems provided herein may therefore create several possible expansions for the sig codes, each representing a different interpretation of the sig. The result of pre-processing is one or more strings, each representing a different interpretation of the input text. Each such string is called a "normalized string." The processor 304 may utilize a machine learning model to perform one or more of the above described tasks, without limitation. A machine learning model may be used to output one or more sigs based on received input text. A machine learning model may be trained with training data correlating input text to one or more sigs, training data correlating input text to correct spelling, punctuation, expanded abbreviations, and/or other forms of text. Training data may be received through user input, external computing devices, and/or previous iterations of processing. A machine learning model may additionally or alternatively be used to input text and output corrected text, such as corrected spelling, normalizing punctuations, normalizing cases, expanding abbreviations, and the like. A machine learning model may be as described below with reference to FIG. 6.

In step 204, the processor 304 identifies a portion or portions ("substring(s)") of the input text to be replaced with a corresponding semantic structure (also identified herein as "STRUCs"). For example, the above instruction S can be broken down into three portions, such as "take 2 tablets now," "take 1 tablet in the morning for 2 weeks," and "take 2 tablets before bedtime." In step 206, each of these portions is replaced with a corresponding semantic structure STRUC by the processor 304. The processor 304 may utilize a machine learning model to break down one or more instructions into one or more portions or STRUCs. A machine learning model may be trained with training data correlating instructions to STRUCs. Training data may be received through user input, external computing devices, and/or previous iterations of processing. A machine learning model may be configured to input instructions and output one or more STRUCs. Semantic structures represent various types of information in the prescription, such as dose, frequency, directive, periodicity, tapering, and the like. The processor recursively applies rules to the substring that replace sequences of text with structures. In some embodiments, because this application of rules is performed more than one time, some structures are replaced with other structures. For instance, having replaced the numerical information in a string, the text appears as "<<NUM_X>> times a day." The processor can then replace this text with "<<FREQ_101>>". This particular structure, FREQ_101, has a property "Quant" (short for quantity) with assigned value "NUM_X" and property "TimeUnit" with value "day," summarized in the table below:

TABLE 1

Example of a structure with corresponding properties and values.

| STRUC | Property | Value |
|---|---|---|
| FREQ_101 | Quant | NUM_X |
| | TimeUnit | day |

In some embodiments, there may be many different STRUCs, some of them recursively containing other STRUCs. The STRUCs may include any from the following list, although the list does not represent an exhaustive list of STRUCs.

FORM. This structure represents the type of medication, e.g., "tablet," "tablespoonful," "suppository," etc.

DOSE. This structure represents information about the quantity of form of the medication, such as "2-3 puffs," "up to 4 tablets," etc. DOSE has 3 components: QUANT (representing quantity or range of quantities such as "2 to 3"), FORM (see above), and a binary flag "upto" which, if TRUE, indicates that QUANT represents maximal allowable quantity for the dose.

PERIODICITY. This structure represents information about how many time units to wait between dosing events. For example, "every 4-8 hours," "every other day," "every 3rd week." This is different from FREQ which represents how many times per time unit to administer the dose, e.g. "once a week," "up to 3 times a day," etc.). PERIODICITY has 3 components: QUANT (e.g. range of "2 to 3"), TIMEUNIT (e.g. hour, day, week), and a binary flag "upto" which, if TRUE, indicates that QUANT represents minimal allowable period between doses (as in "up to every 8 hours").

TAPER. This structure represents tapering up or down instructions, such as "take 6 tablets by mouth on day 1, then decrease by 1 tablet every 3 days."

DIRECTIVE. This structure represents language directing the patient e.g. "take," "apply," etc.

SUBSTRATE. This structure represents the substrate that is used to mix or to drink the dose with, e.g., "mix 17 g with 8 oz. of water."

ROUTE. This structure represents the route by which to take the medication, e.g., "by mouth," "intramuscularly," etc.

SITE. This structure represents the site where the medication is to be applied, e.g., in "use 2 sprays to each nostril," "each nostril" is the site of administration.

VEHICLE. This structure represents the vehicle of drug administration, e.g., "via nebulizer."

TIMING. This structure indicates the timing of drug administration, e.g., "before meals," "2 hours after breakfast," etc.

FREQ. This structure represents the frequency of administration, e.g., "2 times daily."

DURATION. This structure represents the duration of treatment with the medication, e.g., "take for 3 days," "take for the next 3 days," "for 3 more days," etc.

INDICATION. This structure represents the condition for which the drug prescribed, e.g., "severe abdominal pain," "to reduce pain or fever," etc.

AS_NEEDED. This structure represents directive modifiers such as "as needed" and "only if needed."

STOP_CONDITION. This structure represents the condition which triggers discontinuation of using the medication or stopping tapering, e.g., "until gone" or "to effect."

IF_CONDITION. This structure represents the condition which triggers additional actions to take upon certain symptoms or events occurring, such as "if dizziness occurs stop taking immediately and call a doctor".

FOLLOW_UP_CONDITION: In patient discharge instructions, this structure represents a condition when the patient should follow up with the clinic, e.g. "if experiencing nausea", "if fever over 103F", etc.

FOLLOW_UP_DIRECTION: In patient discharge instructions, this structure represents direction who the patient should follow up with, e.g. emergency department, primary care provider, surgery department, etc.

FOLLOW_UP_TIMING: In patient discharge instructions, this structure represents when the patient should follow up, e.g. "in 2 days", "within 1-2 weeks", etc.

The result of exemplary step 206 is that the instruction $S_{norm}$ is replaced with different sequences of STRUCs representing the semantic structures of $S_{norm}$. In some embodiments, if there is some unprocessed or unrecognized text left over in the instruction $S_{norm}$ after applying known rules, these substrings can be removed from further processing. The processor 304 can use regular expression pattern matching for identifying STRUCs and recursively assembling them. In some embodiments, the processor 304 may utilize a machine learning model to identify and recursively assembly one or more STRUCs. For instance, a machine learning model may be trained with training data correlating unprocessed and/or unrecognized text to one or more STRUCs. Training data may be received through user input, external computing devices, and/or previous iterations of processing.

Figure 4:
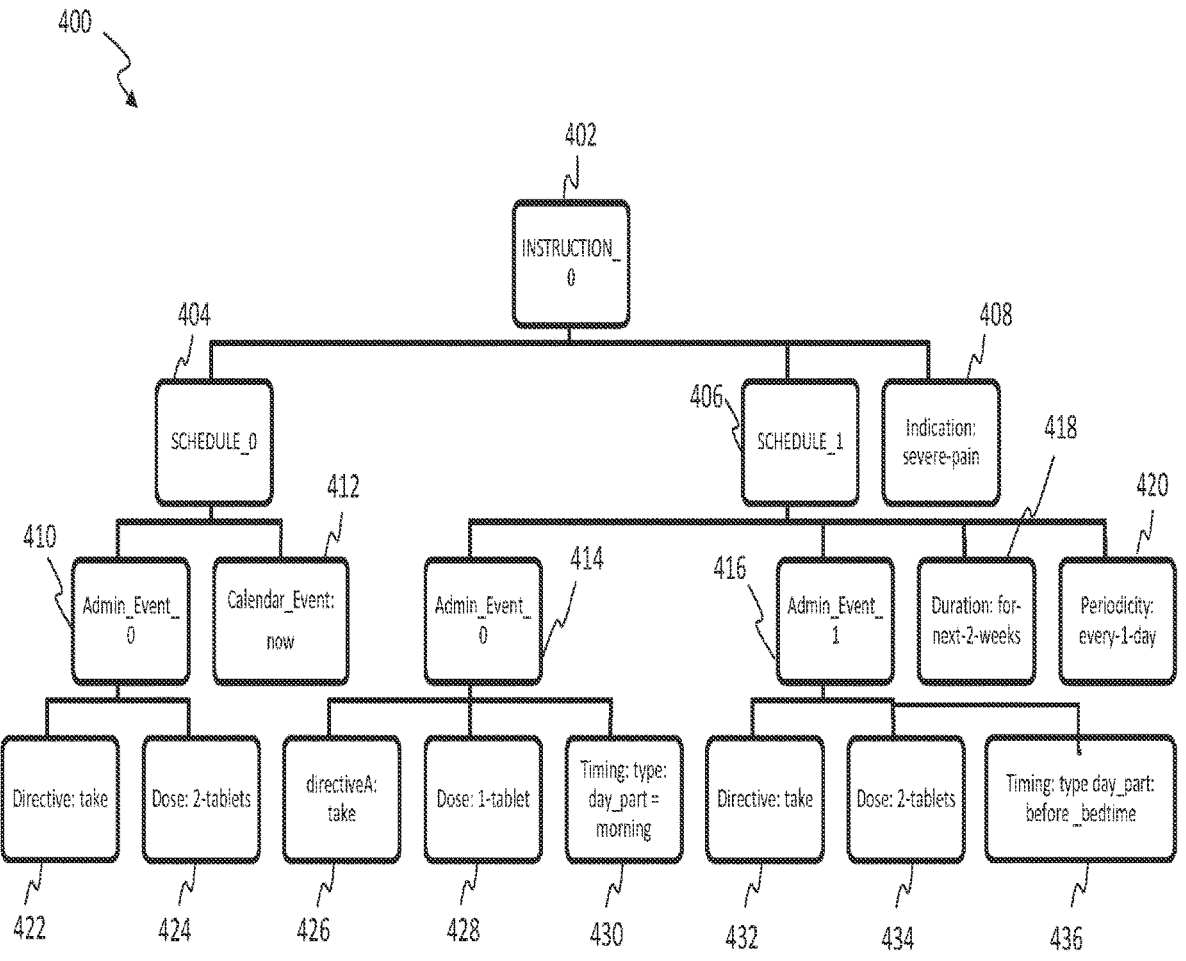
FIG. 4 is a diagram of an exemplary embodiment of a semantic tree representation of a medical prescription.

Once replaced, in step 208, the at least one semantic structure can be organized into a semantic tree (also referred to herein as "SEM"). Processor 304 can apply pattern matching techniques to a sequence of structures (STRUCs) via regular expressions to create a semantic tree (SEM) that represents the scheduling during the day and between days of prescriptive directions. Processor 304 may additionally or alternatively utilize a machine learning model to organize one or more semantic structures into a semantic tree. A machine learning model may be trained with training data correlating semantic structures to semantic trees. Training data may be received through user input, external computing devices, and/or previous iterations of processing. A machine learning model may be trained and/or configured to input semantic structures and output semantic trees. A semantic tree represents the interlingual meaning of the input text, in this case, the directions for use of medication. The tree architecture is typically independent of the order of presentation or surface properties of the words in the instruction S. An example of the above instruction S organized in semantic structures and semantic tree is provided in FIG. 4. FIG. 4 is a diagram of an exemplary embodiment of a semantic tree 400 representation of the medical instruction 402 above. Note that a semantic tree can include one or more instructions. An instruction S can be made up of one or more multiple drug administration regimes or schedules. Exemplary instruction S ("INSTRUCTION_0") 402 includes a first schedule ("SCHEDULE_0") 404 and a second schedule ("SCHEDULE_1") 406, in addition to an indication 408:

SCHEDULE_0 (404): take 2 tablets now

SCHEDULE_1 (406): then every day for the next 2 weeks, take 1 tablet in the morning and 2 tablets before bedtime Indication (408): for severe pain Instruction S may also include other properties such as "as_needed," which modifies the directive (see above for details). The schedules 404, 408 can each include administration structures ("Admin_Event"), which represent directions to use a medication at a given time (e.g., "take 1 tablet in the morning"). Each administrative structure has certain properties, such as: directive, dose, route, site, vehicle, timing, substrate, and the like (see above for definitions of such properties). For example, the prescription "take 1 tab by mouth" may be represented by an administration structure having the properties dose="1 tab," directive="take," and/or route="by mouth." In addition to the administration structures, a schedule may also have temporal substructures and/or properties such as duration, periodicity, frequency, etc. (see above for definitions of such properties).

Thus, the schedules 404, 406 are further divided into the following structures:

directive can be deduced to be "take." In some embodiments, the processor 304 may utilize a machine learning model to modify the semantic tree. For instance, a machine learning model may be trained with training data correlating semantic trees to modified semantic trees, such as with directives, drug form, and the like. Training data may be received through user input, external computing devices, and/or previous iterations of processing.

In some embodiments, the deduction can be pre-programmed and based, for example, on a statistical analysis of a corpus of historical prescriptions using machine learning techniques. For instance, a machine learning model, such as described below with reference to FIG. 6 may be used to improve deduction, translation, paraphrasing, and the like of one or more semantic structures from a source language to a target language. A machine learning model used by the system may be trained to input text and output translations of text, such as without limitation one or more paraphrases. Training data may be received through user input, external computing devices, and/or previous iterations of processing. For instance, previous inputs and outputs of the system may be used as training data for a machine learning model. In some embodiments, iterations of implementation of the system may be used as training data. A machine learning model may input text, semantic structures, and the like and output paraphrases, deductions, or other outputs. In some embodiments, a guess may be made as to the directive and one or more translations may be created from the same instruction. For example, if the instruction is "twice daily as needed," the possible directives could be "take" (if the form is a tablet or a capsule), "apply" if the form is a nicotine patch, or "insert" if the form is a suppository. In step 214 (discussed in more detail below), the user of the system (such as the pharmacist or doctor) can select which "guess" or paraphrase is the right one for the specific instruction he or she intended when entering the input text into the user interface 302. In some embodiments, a guess may be calculated through a machine learning model, such as described above.

In step 210, some or all of the semantic tree 400 of the instruction 402 is matched to a phrase or phrases from a phrase bank stored in storage 310 coupled to processor 304.

TABLE 2

Example of an instruction divided into semantic structure forming the semantic tree of FIG. 4.

| | Sublevel 1 | Sublevel 2 | Sublevel 3 | Value |
|---|---|---|---|---|
| INSTRUCTION_0 (402) | SCHEDULE_0 (404) | Admin_Event_0 (410) | Directive (422) | take |
| | | | Dose (424) | 2-tablets |
| | | | Calendar_Event (412) | now |
| | SCHEDULE_1 (406) | Admin_Event_0 (414) | directiveA (426) | take |
| | | | Dose (428) | 1-tablet |
| | | | Timing (430) | morning |
| | | Admin_Event_1 (416) | Directive (432) | take |
| | | | Dose (434) | 2-tablets |
| | | | Timing (436) | before_bedtime |
| | | Duration (418) | | next-2-weeks |
| | | Periodicity (420) | | every-1-day |
| | | Indication (408) | | severe-pain |

In some embodiments, after organizing the structures into a tree, the processor 304 modifies the semantic tree in various ways, such as its directives, drug form, and the like. This improves the translation process because, in many instances, instructions may be missing information or some of the information is implicit. For example, if the instruction is "1 tablet daily," lacks a directive on its face, but the The phrase bank includes phrases that are pre-translated into a number of different languages and can be referenced by the processor. These pre-translated phrases are verified and cross-checked by multiple translators, including certified subject-matter experts (e.g., pharmacists), to lower the probability of mistranslation. Because there are a finite number of phrases commonly used in most contexts (prescribing medication for instance, on the order of thousands), the phrase bank can be of a manageable size for storage purposes and minimal in the use of computational resources and/or efficiency in speed of returning a translation. Note that for other industries, a phrase bank may be different sizes.

The translations of these phrases are verified and cross-checked by multiple translators (for instance, for medical prescription translation, the translators include certified pharmacists) to make the probability of mistranslation arbitrarily low. The translation of these phrases between a source language and a target language is accomplished through a translation process involving back-translation and reconciliation of back-translation with the input. The phrases are translated and compiled into the phrase bank prior to deployment of the system. Note that each phrase is preferably unambiguous and, further, the meaning of each phrase does not depend on its context or adjacent phrases. In other words, the commutative property applies to a sequence of phrases in the following manner $$\text{Translation}([p_1+p_{2+} \ldots +p_n])=[\text{Translation}(p_1)+ \\ \text{Translation}(p_2)+ \ldots +\text{Translation}(p_n)]$$

where $p_1, p_2, \ldots p_n$ are phrases in a the source language, the plus sign "+" represents the concatenation of the phrases, and the "Translation" function maps the phrases from the source language to the target language. Note, however, that the commutative property does not necessarily hold at the level of single words within the phrases. Naturally, the relationships between single words in a phrase are different for different languages (due to grammatical differences) to express the same meaning. There may be other concerns in translating to a particular language. For instance, in some languages such as Russian, verbs have grammatical gender. Thus, in a diplomatic setting, a translation of "The Secretary of State delivered a powerful speech to the United Nations Assembly" will be different for a female or male Secretary of State. Thus, the phrases are determined such that they can be arranged in in any order at runtime without validation from a linguist.

Note that the portions of the tree 400 that are ultimately matched to a phrase may be the portion under instruction 402, a portion representing one or more schedules 404, 406, a portion under one or more administration events 410, 414, 416, and the like. In the matching process, processor 304 identifies the version(s) of a phrase and ensures that these versions each cover the meaning of each semantic structure in the portion of the tree 400 selected for matching. One technique includes determining all possible partitions of the semantic structures in a particular instruction 402 or a portion of an instruction 402 and create groups of structures. However, this is a computationally intensive exercise—only 7 structures results in 877 partitions of the set of structures to test against the phrase bank; for 8 structures that number increases to 4140 partitions one would have to test against the phrase bank. In some instances, a particular structure (often a directive) can repeat in multiple phrases, using up computational resources. An example of this "Take 1 tablet once daily," in which the semantic structures are: DIRECTIVE DOSE FREQ PERIODICITY, compared to "Take this medicine every day," in which the semantic structures are: DIRECTIVE ANAPHORA PERIODICITY.

Thus, to minimize the search space, various heuristic approaches may be used, such as only matching phrases from the phrase bank that do not have any contradictory properties to the corresponding properties of the instruction S. For example, if the instruction S has the form "puff" then the processor would not match any phrases where the form is "tablet." After determining potential versions, the versions are ranked. One example of ranking may be based on inclusion of the semantic structures in the instruction S. Another way to rank is the "smoothness" of the versions. For instance, if two versions have comparable inclusions of the structures but a first version has only two strings to accomplish the intended meaning and the other version has three strings, the two-string version is ranked higher. In some embodiments, the best four or less versions may be used for presenting to the user, via the user interface 302. Having determined the list of versions that correspond to the meaning of the instruction S, the numerical placeholders are substituted with their original values. In other words, in the example instruction above, placeholders in S norm are replaced with their corresponding values in S. In some embodiments, comparisons between matching phrases may be ranked through a machine learning model. For instance, a machine learning model may be trained with training data correlating phrases to matching phrases of a phrase bank. Training data may be received through user input, external computing devices, and/or previous iterations of processing. A machine learning model may be trained and/or configured to input phrases and output matching phrases of a phrase bank.

In step 212 of the method 200, the user interface provides one or more versions of the instruction S in the source language to the user. For example, if a single version is provided, the user views the version and can determine if the translation is accurate. If so, the user approves the translation as accurate. If the user determines that the version is not accurate or appropriate, a second version can be presented with alternative instructions S. The process can be repeated until the user confirms an accurate version.

In some instances, multiple (e.g., two or more) versions can be presented simultaneously such that the user can compare the versions and select the one that is most accurate. Thus, if two versions are provided, the versions of the instruction S above may be:

Version 1: Take 1 tablet(s) 1 to 2 times a day. Take daily by mouth. Use this medicine as needed to reduce severe pain.

Version 2: Take 1 tablet by mouth. Take this medicine 1 to 2 times a day. Take this medicine every day. Use this medicine as needed to reduce severe pain.

If the user finds any one of these versions to adequately reflect the meaning of instruction S, then the user can select and confirm the desired version along with a target language. In some embodiments, if the user does not find any version suitable, the user may reject the presented versions or provide a modified input text to the user interface. In some instances, only a single version may be presented to the user, who in turn can confirm that the version is a desired translation, or, alternatively, reject the version and be presented with another (or others).

Figure 5:
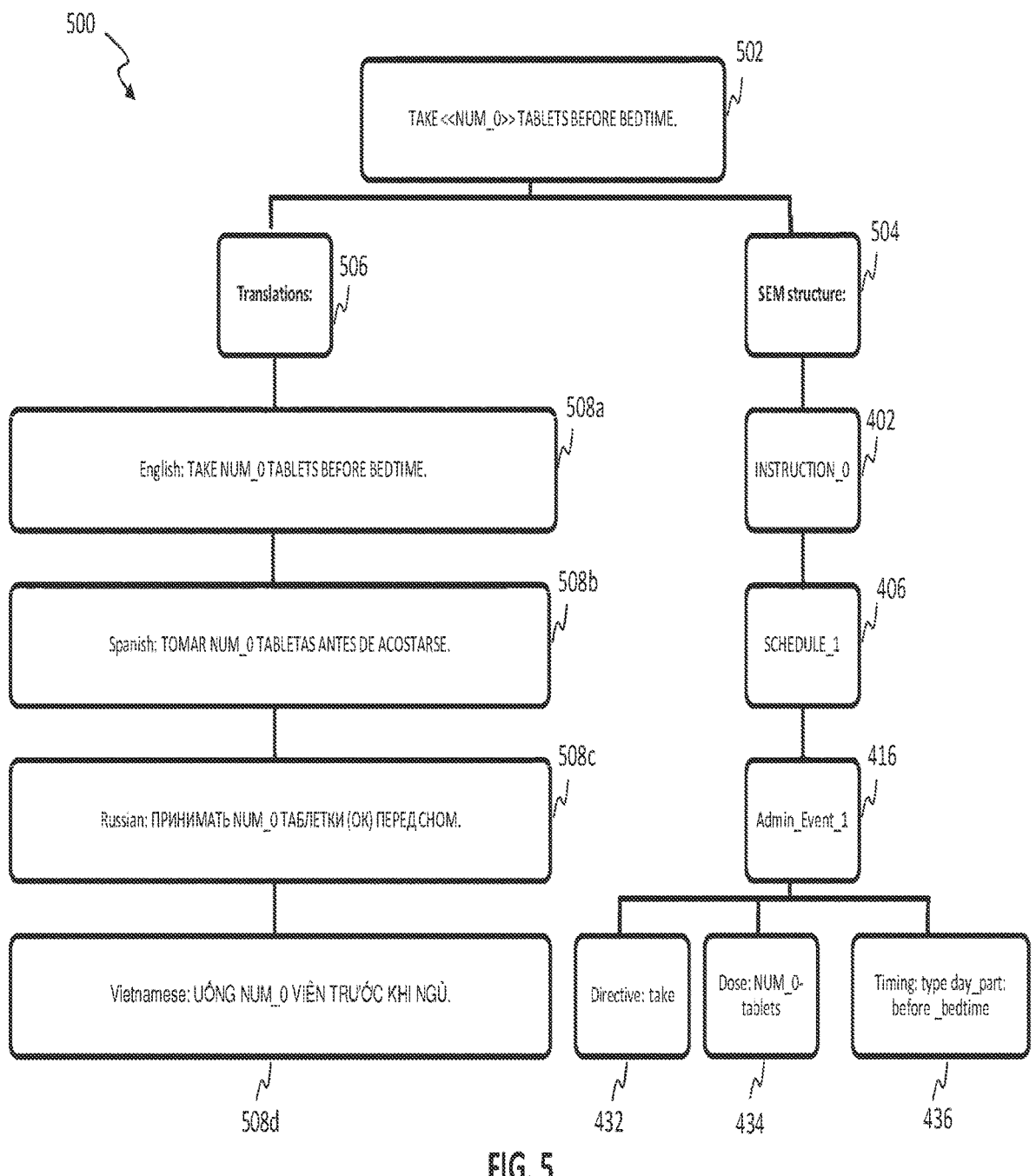
FIG. 5 is a diagram of an exemplary embodiment of a structure of a phrase selected from a phrase bank.

At this time, the process may start over again and/or be modified to check for other versions to present to the user. Once a user selects an adequate version and at least one target language, the user interface receives the user's selections. In step 216, the selected version is then translated from the source language into the selected target language. The processor 304 looks up the translation of the phrases in the selected version in the target language and instantiates any numerical placeholders with the values from the original instruction. If there are two or more phrases, the processor 304 then concatenates the translated phrases. FIG. 5 is a diagram 500 of an exemplary embodiment of a phrase 502 selected from a phrase bank. In the right branch is the semantic tree structure 504 of one of the phrases from the instruction 402. Specifically, the phrase is "Take <<NUM_0>> tablets before bedtime." In the left branch are the one or more translations 508a-508d of this particular phrase:

English 508a: TAKE NUM_0 TABLETS BEFORE BED-TIME.

Spanish 508b: TOMAR NUM_0 TABLETAS ANTES DE ACOSTARSE.

Russian 508c: ПР *ИНИ*МАТ Ь NUM_0 ТА *БЫ*IET *КИ* (О *К*) ПЕРЕ *ЕД* CHOM.

Vietnamese 508d: U ỐNG NUM_0 VIÊN TRU ỐC KHI NGU.

In step 218, the processor 304 provides the user interface 302 with selected version of the instruction S in the target language. Thus, the user, such as a pharmacist, would be presented with a reliable translation of the original input in near real-time to be able to effectively communicate the prescription to his or her patient.

In some embodiments, one or more processes described herein may be passed from the processor 304 to a server system 312. For example, the user interface 302 can be in the form of an app on a mobile device and the processor can be the processor of the mobile device. In such a case, the mobile device may transmit (via wireless or wired communication) to an external server system 312. The external server 312 can process some or all of the input from the user interface 302 and return the translation. In some embodiments, the processor 304 may utilize a machine learning model. A machine learning model may be trained with training data in the form of input text and paraphrases corresponding to the input text that may have been selected by one or more users. A machine leaning model may include a large language model (LLM) or other language model. A machine learning model may input text and output one or more phrases of the input text in a target language. A machine learning model may be trained and/or configured to receive input text and output STRUCs corresponding to the input text. A machine learning model may compare text to one or more possible partitions of the text, may compare text to phrases in a phrase bank, may rank potential translated phrases of input text, and may be used in any computational process as described throughout this disclosure, without limitation.

Additional Embodiments

Although examples of the system described above relate to pharmaceutical instructions, other fields may be applicable. For instance, the system may be used for medical instructions, such as pharmaceutical instructions as described above, hospital discharge instructions, hospital or clinic communications, emergency evacuation instructions, European Union Clinical Trials Regulation (EU CTR) requests for information (RFIs), drug labels and medical device labels, and/or other medical instructions.

Hospital discharge instructions may include words, phrases, and/or sentences relating to a discharge of a patient from a hospital. Hospital discharge instructions may include instructions relating to specific body parts, such as, but not limited to, feet, hands, arms, legs, stomach, back, shoulders, head, and the like. Hospital discharge instructions may include instructions relating to one or more medicines, such as, without limitation, quantities to be taken, frequencies of medicine to be taken, warning symptoms, and/or other instructions. Hospital discharge instructions may include instructions on what to do if symptoms persist or worsen, such as calling a doctor, increasing pain medication, and the like. Hospital instructions may include activity based instruction such as resting certain body parts, not applying pressure to certain body parts, avoiding bright lights or loud sounds, engaging in physical therapy, and/or other instructions. They may include information on potential complications ("you might experience nausea and fatigue"), instructions for follow up ("follow up with your primary care provider within 2 weeks after discharge"), etc. For instance and without limitation, hospital discharge instructions may include the following: "Avoid peroxide for incisions closed with absorbable suture. Clean with soap and running water. Call our care provider if you experience nausea or fever over 103F". The systems and methods described above may input text relating to hospital discharge instructions and may output one or more translations of the hospital discharge instructions using methods and processes as described above with reference to FIGS. 1-5. For instance and without limitation, hospital discharge instructions may be broken down into semantic structures such as body part (e.g. "head), directives (e.g. "avoid peroxide), if conditions (e.g. "if headache worsens call doctor"), time periods (e.g. "for the next two weeks"), medication quantity (e.g. "take two 25 mg capsules), medication frequency ("take two capsules daily"), symptoms (e g dizziness, fatigue, cough), follow up directions ("follow up with your surgery team"), follow up timing ("2 days after discharge"), follow up conditions ("if nausea persists"), and the like. Semantic structures of hospital discharge instructions may be organized into a semantic tree and may be translated via a phrase bank, as described above and without limitation.

Hospital or clinic communications may include words, phrases, and/or sentences relating to communications between patients and/or families and hospital staff, hospital staff to hospital staff, and/or other communications. Hospital or clinic communications may include one or more directives for a patient, family, and the like. Directives may include waiting instructions, directions on how to arrive at a room, preparation instructions for operations, and the like. For instance, hospital or clinic communications may include the following: "I will be taking you for x-rays in 30 minutes. Please do not drink water until then". The systems and methods described above may input text relating to hospital or clinic communications and may output one or more translations of the hospital or clinic communications using methods and processes as described above with reference to FIGS. 1-5. For instance hospital or clinic communications may be broken down into semantic structures such as, but not limited to, operation (e.g. x-rays, surgery, etc.), time period (e.g. "in 30 minutes"), negative directives (e.g. "do not drink water"), positive directives (e.g. "leave metal outside the room"), and the like. Semantic structures of hospital or clinic communications may be organized into a semantic tree and may be translated via matching of a phrase bank, as described above and without limitation.

Emergency evacuation instructions may include words, phrases, and/or sentences relating to evacuation of a room, hospital, or other building. For instance, evacuation instructions may include directions to a nearest exit, instructions on what to do if an exit is blocked, and/or other instructions. For example, emergency evacuation instructions may include the following phrase: "2$^{nd}$ and 3$^{rd}$ floor: proceed to the East wing and take the stairs down. Don't use the elevators. Ground floor: exit through the cafeteria." The systems and methods described above may input text relating to emergency evacuation instructions and may output one or more translations of the emergency evacuation instructions using methods and processes as described above with reference to FIGS. 1-5. For instance, emergency evacuation instructions may be broken down into semantic structures such as, but not limited to, locations (e.g. "third floor"), directions (e.g. "head west"), negative directives (e.g. "do not take elevator"), relative directions (e.g. "if on ground floor head east"), and the like. Semantic structures of emergency evacuation instructions may be organized into a semantic tree and may be translated via matching of a phrase bank, as described above and without limitation.

EU CTR RFI's may include RFI's for clinical trials of new drugs, medical devices, procedures, and/or other trials. For instance and without limitation, RFI's may include questions pertaining to control groups, dosages of medications, test variables, and/or other information. As a non-limiting example, a pharmaceutical company may need to respond to one or more RFI's such as information regarding a demographic of a control group of a trial. The systems and methods described above may input text of an RFI and may output one or more translations of the RFI, using methods and processes as described above with reference to FIGS. 1-5. For instance, RFIs may be broken down into semantic structure such as, but not limited to, populations (e.g. "what was the trial group?"), medication dosage (e.g. "10 uL"), time periods (e.g. "how long did the trial go on for?"), trial variables (e.g. "what placebo was used?"), trial results (e.g. "what was the outcome?"), and the like. Semantic structures of RFIs may be organized into a semantic tree and may be translated via matching of a phrase bank, as described above and without limitation.

Drug labels may include, without limitation, quantities of medicine, warning of interactions with other medicine, usage instructions, how not to use, how to store, when to call the doctor, and/or other information. The systems and methods described above may input text of one or more drug labels and output one or more translations of the drug labels using methods and processes as described above with reference to FIGS. 1-5. For instance, drug labels may be broken down into semantic structures such as, but not limited to, administration directions (e.g. "take with food"), drug quantities (e.g. "10 mg"), storage directions (e.g. "keep dry"), side effects (e.g. "fatigue"), drug interaction information (e.g. "do not drink alcohol"), emergency instructions (e.g. "if burning sensation occurs call doctor immediately"), warnings (e.g. "this medication can cause fatigue, do not operate heavy machinery"), and the like. Semantic structures of drug labels may be organized into a semantic tree and may be translated via matching of a phrase bank, as described above and without limitation.

Medical device instructions may include usage instructions, warnings, troubleshooting guides, operational guides, device indicator meanings such as light emitting diode (LED) meanings, and/or other information. Medical devices may include, but are not limited to, respiratory devices, hearing aids, insulin injection devices, or any other medical device. The systems and methods described above may input instructions relating to a medical device and may output one or more translations of the instructions using methods and processes as described above with reference to FIGS. 1-5. For instance and without limitation, medical device instructions may be broken down into semantic structures such as operational actions (e.g. "place mask on nose"), time periods (e.g. "let machine run for 10 minutes"), maintenance instructions (e.g. "wash with water only"), warnings (e.g. "this product contains a lithium-ion battery, keep away from extreme temperatures"), storage information (e.g. "keep out of direct sunlight"), and the like. Semantic structures of medical device instructions may be organized into a semantic tree and may be translated via matching of a phrase bank, as described above and without limitation.

The system may receive input text relating to any of the medical instructions described throughout this disclosure in a source language and provide translations of the input text in one or more target languages, such as described above with reference to FIGS. 1-5.

Figure 6:
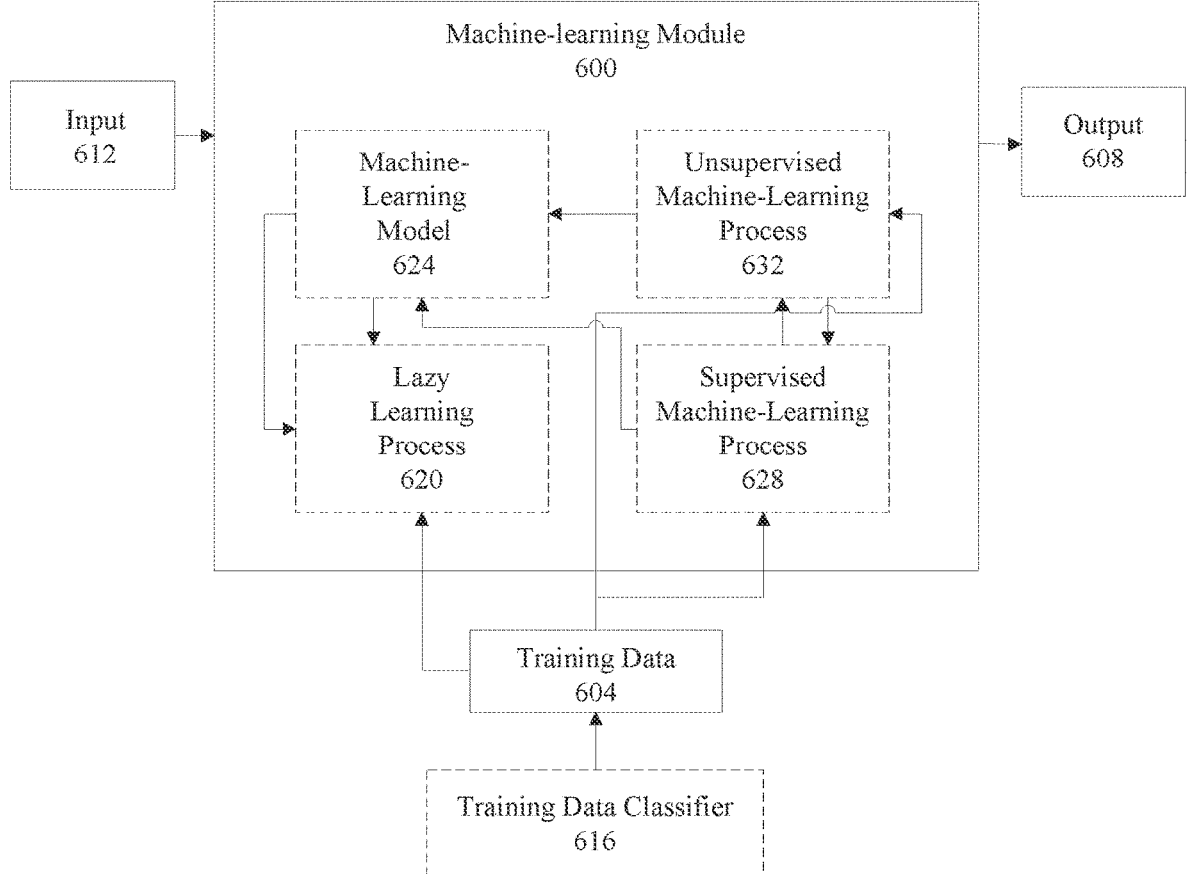
FIG. 6 is a block diagram of an exemplary embodiment of a machine learning module.

FIG. 6 illustrates an exemplary embodiment of a machine-learning module 600 that may perform one or more machine-learning processes as described herein. Machine-learning module 600 may be configured to perform various determinations, calculations, processes and the like as described in this disclosure using a machine-learning process. A "machine learning process," as used in this disclosure, is a process that automatedly uses training data to generate an algorithm that calculates outputs given data as inputs. A machine learning process contrasts to a non-machine learning software program where the commands to be executed are determined in advance by a user and written in a programming language.

Still referring to FIG. 6, machine learning module 600 may utilize training data 604. "Training data," as used herein, refers to data containing correlations that a machine-learning process may use to model relationships between two or more categories of data elements. For instance, and without limitation, training data 604 may include a plurality of data entries, each entry representing a set of data elements that were recorded, received, and/or generated together. Training data 604 may include data elements that may be correlated by shared existence in a given data entry, by proximity in a given data entry, or the like. Multiple data entries in training data 604 may demonstrate one or more trends in correlations between categories of data elements. For instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 604 according to various correlations. Correlations may indicate causative and/or predictive links between categories of data elements, which may be modeled as relationships such as mathematical relationships by machine-learning processes as described in further detail below. Training data 604 may be formatted and/or organized by categories of data elements. Training data 604 may, for instance, be organized by associating data elements with one or more descriptors corresponding to categories of data elements. As a non-limiting example, training data 604 may include data entered in standardized forms by one or more individuals, such that entry of a given data element in a given field in a form may be mapped to one or more descriptors of categories. Elements in training data 604 may be linked to descriptors of categories by tags, tokens, or other data elements. Training data 604 may be provided in fixed-length formats, formats linking positions of data to categories such as comma-separated value (CSV) formats and/or self-describing formats. Self-describing formats may include, without limitation, extensible markup language (XML), JavaScript Object Notation (JSON), or the like, which may enable processes or devices to detect categories of data.

With continued reference to refer to FIG. 6, training data 604 may include one or more elements that are not categorized. Uncategorized data of training data 604 may include data that may not be formatted or containing descriptors for some elements of data. In some embodiments, machine-learning algorithms and/or other processes may sort training data 604 according to one or more categorizations. Machine-learning algorithms may sort training data 604 using, for instance, natural language processing algorithms, tokenization, detection of correlated values in raw data and the like. In some embodiments, categories of training data 604 may be generated using correlation and/or other processing algorithms. As a non-limiting example, in a body of text, phrases making up a number "n" of compound words, such as nouns modified by other nouns, may be identified according to a statistically significant prevalence of n-grams containing such words in a particular order. For instance, an n-gram may be categorized as an element of language such as a "word" to be tracked similarly to single words, which may generate a new category as a result of statistical analysis. In a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 604 to be made applicable for two or more distinct machine-learning algorithms as described in further detail below. Training data 604 used by machine-learning module 600 may correlate any input data as described in this disclosure to any output data as described in this disclosure, without limitation.

Further referring to FIG. 6, training data 604 may be filtered, sorted, and/or selected using one or more supervised and/or unsupervised machine-learning processes and/or models as described in further detail below. In some embodiments, training data 604 may be classified using training data classifier 616. Training data classifier 616 may include a classifier. A "classifier" as used in this disclosure is a machine-learning model that sorts inputs into one or more categories. Training data classifier 616 may utilize a mathematical model, neural net, or program generated by a machine learning algorithm. A machine learning algorithm of training data classifier 616 may include a classification algorithm. A "classification algorithm" as used in this disclosure is one or more computer processes that generate a classifier from training data. A classification algorithm may sort inputs into categories and/or bins of data. A classification algorithm may output categories of data and/or labels associated with the data. A classifier may be configured to output a datum that labels or otherwise identifies a set of data that may be clustered together. Machine-learning module 600 may generate a classifier, such as training data classifier 616 using a classification algorithm. Classification may be performed using, without limitation, linear classifiers such as without limitation logistic regression and/or naive Bayes classifiers, nearest neighbor classifiers such ask-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 616 may classify elements of training data to educational data.

Still referring to FIG. 6, machine-learning module 600 may be configured to perform a lazy-learning process 620. Lazy-learning process 620 may include a "lazy loading" or "call-when-needed" process and/or protocol. A "lazy-learning process" may include a process in which machine learning is performed upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 604. Heuristic may include selecting some number of highest-ranking associations and/or training data 604 elements. Lazy learning may implement any suitable lazy learning algorithm, including without limitation a K-nearest neighbors algorithm, a lazy naive Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Still referring to FIG. 6, machine-learning processes as described in this disclosure may be used to generate machine-learning models 624. A "machine-learning model" as used in this disclosure is a mathematical and/or algorithmic representation of a relationship between inputs and outputs, as generated using any machine-learning process including without limitation any process as described above, and stored in memory. For instance, an input may be sent to machine-learning model 624, which once created, may generate an output as a function of a relationship that was derived. For instance, and without limitation, a linear regression model, generated using a linear regression algorithm, may compute a linear combination of input data using coefficients derived during machine-learning processes to calculate an output. As a further non-limiting example, machine-learning model 624 may be generated by creating an artificial neural network, such as a convolutional neural network comprising an input layer of nodes, one or more intermediate layers, and an output layer of nodes. Connections between nodes may be created via the process of "training" the network, in which elements from a training data 604 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 6, machine-learning algorithms may include supervised machine-learning process 628. A "supervised machine learning process" as used in this disclosure is one or more algorithms that receive labelled input data and generate outputs according to the labelled input data. For instance, supervised machine learning process 628 may include input text as described above as input, matching phrases as outputs, and a scoring function representing a desired form of relationship to be detected between inputs and outputs. A scoring function may maximize a probability that a given input and/or combination of elements inputs is associated with a given output to minimize a probability that a given input is not associated with a given output. A scoring function may be expressed as a risk function representing an "expected loss" of an algorithm relating inputs to outputs, where loss is computed as an error function representing a degree to which a prediction generated by the relation is incorrect when compared to a given input-output pair provided in training data 604. Persons skilled in the art, upon reviewing the entirety of this disclosure, will be aware of various possible variations of at least a supervised machine-learning process 528 that may be used to determine relation between inputs and outputs. Supervised machine-learning processes may include classification algorithms as defined above.

Further referring to FIG. 6, machine learning processes may include unsupervised machine-learning processes 632. An "unsupervised machine-learning process" as used in this disclosure is a process that calculates relationships in one or more datasets without labelled training data. Unsupervised machine-learning process 632 may be free to discover any structure, relationship, and/or correlation provided in training data 604. Unsupervised machine-learning process 632 may not require a response variable. Unsupervised machine-learning process 632 may calculate patterns, inferences, correlations, and the like between two or more variables of training data 604. In some embodiments, unsupervised machine-learning process 632 may determine a degree of correlation between two or more elements of training data 604.

Still referring to FIG. 6, machine-learning module 600 may be designed and configured to create a machine-learning model 624 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of I divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 6, machine-learning algorithms may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include various forms of latent space regularization such as variational regularization. Machine-learning algorithms may include Gaussian processes such as Gaussian Process Regression. Machine-learning algorithms may include cross-decomposition algorithms, including partial least squares and/or canonical correlation analysis. Machine-learning algorithms may include naive Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

The term "system" may encompass all apparatus, devices, and machines for processing data, including by way of example a programmable processor, a computer, or multiple processors or computers. A processing system can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, executable logic, or code) can be written in any form of programming language, including compiled or interpreted languages, or declarative or procedural languages, and it can be deployed in any form, including as a standalone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

Computer readable media suitable for storing computer program instructions and data include all forms of non-volatile or volatile memory, media and memory devices, including by way of example semiconductor memory devices, e.g., EPROM, EEPROM, and flash memory devices; magnetic disks, e.g., internal hard disks or removable disks or magnetic tapes; magneto optical disks; and CD-ROM and DVD-ROM disks. The processor and the memory can be supplemented by, or incorporated in, special purpose logic circuitry. Sometimes a server (e.g., forming a portion of the server 102) is a general purpose computer, and sometimes it is a custom-tailored special purpose electronic device, and sometimes it is a combination of these things.

Implementations can include a back end component, e.g., a data server, or a middleware component, e.g., an application server, or a front end component, e.g., a client computer having a graphical user interface or a Web browser through which a user can interact with an implementation of the subject matter described is this specification, or any combination of one or more such back end, middleware, or front end components. The components of the system can be interconnected by any form or medium of digital data communication, e.g., a communication network. Examples of communication networks include a local area network ("LAN") and a wide area network ("WAN"), e.g., the Internet.

Certain features that are described above in the context of separate implementations can also be implemented in combination in a single implementation. Conversely, features that are described in the context of a single implementation can be implemented in multiple implementations separately or in any sub-combinations.

The order in which operations are performed as described above can be altered. In certain circumstances, multitasking and parallel processing may be advantageous. The separation of system components in the implementations described above should not be understood as requiring such separation.

The terms and expressions employed herein are used as terms and expressions of description and not of limitation and there is no intention, in the use of such terms and expressions, of excluding any equivalents of the features shown and described or portions thereof. In addition, having described certain embodiments of the invention, it will be apparent to those of ordinary skill in the art that other embodiments incorporating the concepts disclosed herein may be used without departing from the spirit and scope of the invention. The structural features and functions of the various embodiments may be arranged in various combinations and permutations, and all are considered to be within the scope of the disclosed invention. Unless otherwise necessitated, recited steps in the various methods may be performed in any order and certain steps may be performed substantially simultaneously. Accordingly, the described embodiments are to be considered in all respects as only illustrative and not restrictive. Furthermore, the configurations described herein are intended as illustrative and in no way limiting. Similarly, although physical explanations have been provided for explanatory purposes, there is no intent to be bound by any particular theory or mechanism, or to limit the claims in accordance therewith.

What is claimed is:

1. A computer-implemented method for translating input text of a medical instruction from a source language to a target language, the method comprising:

receiving, by an interface, the input text of the medical instruction in a source language;

identifying, by a processor coupled to the interface, at least one portion of the input text to be replaced with a corresponding semantic structure, the corresponding semantic structure provided in a storage coupled to the processor;

replacing, by the processor, each of the at least one portion with the corresponding sematic structure to produce at least one semantic structure;

organizing, by the processor, the at least one semantic structure into a semantic tree;

matching, by the processor, a portion of the semantic tree to at least one phrase from a stored phrase bank;

translating, by the processor, the at least one phrase from the source language to the target language; and providing, by the interface, the at least one phrase in the target language;

receiving, by the interface, modified input text in the source language;

identifying, by the processor, at least one portion of the modified input text to be replaced with a different corresponding semantic structure, the corresponding semantic structure provided in a storage coupled to the processor;

replacing, by the processor, each of the at least one portion with the corresponding sematic structure to produce at least one semantic structure;

organizing, by the processor, the at least one semantic structure into a different semantic tree;

matching, by the processor, a portion of the semantic tree to at least one phrase from the stored phrase bank;

providing, by the interface, (i) at least one modified version of the at least one phrase in the source language and (ii) at least one target language to translate the at least one modified version;

receiving, by the interface, a selected version of the modified set of versions and a selected target language from the set of target languages;

translating, by the processor, the selected version from the source language to the target language; and providing, by the interface, the selected version in the target language.

2. The method of claim 1, further comprising:

receiving, at the interface, speech from a user through a microphone of the interface; and converting, by the processor, the speech from a user into the input text.

3. The method of claim 1, wherein the medical instruction are one of hospital discharge instructions, emergency evacuation instructions, or hospital to patient communications.

4. The method of claim 1, further comprising:

replacing, by the processor, numerical information in the input text with corresponding variables; and replacing, by the processor, the corresponding variables with the numerical information.

5. The method of claim 1, further comprising:

providing the input text to a machine learning model;

identifying, by the machine learning model, at least a portion of the input text; and replacing, by the machine learning model, the at least a portion of the input text with a corresponding semantic structure.

6. The method of claim 1, further comprising:

providing, by the interface, a set of target languages to translate the at least one phrase;

receiving, by the interface, the selected target language from the set of target languages; and translating, by the processor, the at least one phrase from the source language to the selected target language.

7. The method of claim 1, further comprising providing, by the interface, (i) one or more versions of the at least one phrase in the source language and (ii) a set of target languages to translate the at least one phrase; and:

providing, by the interface, (iii) an option to decline the one or more versions.

8. The method of claim 1, further comprising:

receiving the input text of a medical instruction at a machine learning model; and matching, by the machine learning model, the input text to the at least one phrase of the phrase bank.

9. The method of claim 8, wherein the matching, by the machine learning model, further comprises:

ranking at least two phrases from the phrase bank to each other; and selecting at least one phrase from the at least two phrases based on the ranking.

10. A system for translating input text of a medical instruction from a source language into a target language, comprising:

a processor; and an interface coupled to the processor and configured to receive the input text of the medical instruction, wherein the processor is configured to:

identify at least one portion of the input text, the at least one portion corresponding to at least one semantic structure provided in a storage coupled to the processor;

replace the at least one portion with the corresponding sematic structure to produce at least one semantic structure;

organize the at least one semantic structure into a semantic tree;

match a portion of the semantic tree to at least one phrase from a stored phrase bank;

translate the at least one phrase from the source language to the target language; and provide the at least one phrase in the target language to a user through the interface;

receive, by the interface, modified input text in the source language;

identify at least one portion of the modified input text to be replaced with a different corresponding semantic structure, the corresponding semantic structure provided in a storage coupled to the processor;

replace each of the at least one portion with the corresponding sematic structure to produce at least one semantic structure;

organize the at least one semantic structure into a different semantic tree;

match a portion of the semantic tree to at least one phrase from the stored phrase bank;

provide by the interface, (i) at least one modified version of the at least one phrase in the source language and (ii) at least one target language to translate the at least one modified version;

receive, by the interface, a selected version of the modified set of versions and a selected target language from the set of target languages;

translate, by the processor, the selected version from the source language to the target language; and provide, by the interface, the selected version in the target language.

11. The system of claim 10, wherein the system is further configured to:

receive, at the interface, speech from a user through a microphone of the interface; and convert, by the processor, the speech from a user into the input text.

12. The system of claim 10, wherein the medical instruction are one of hospital discharge instructions, emergency evacuation instructions, or hospital to patient communications.

13. The system claim 1, wherein the processor is further configured to:

replace numerical information in the input text with corresponding variables; and replace the corresponding variables with the numerical information.

14. The system of claim 10, wherein the processor is further configured to provide the input text to a machine learning model, wherein the machine learning model is configured to identify at least a portion of the input text and replace the at least a portion of the input text with a corresponding semantic structure.

15. The system of claim 10, wherein the processor is further configured to:

provide a set of target languages to translate the confirmed version to a user through the interface;

receive, through the interface, a selected target language from the set of target languages; and translate the at least one phrase from the source language to the selected target language.

16. The system of claim 10, wherein the processor is further configured to:

provide, by the interface, (i) one or more versions of the at least one phrase in the source language and (ii) a set of target languages to translate a confirmed version; and:

provide, by the interface, (iii) an option to decline the one or more versions.

17. The system of claim 10, wherein the processor is further configured to provide the input text of a medical instruction to a machine learning model, wherein the machine learning model is configured to match the input text to the at least one phrase of the phrase bank.

18. The system of claim 17, the machine learning model is further configured to:

rank at least two phrases from the phrase bank to each other; and select at least one phrase from the at least two phrases based on the ranking.

\* \* \* \* \*